United States Patent
Matsuzaki et al.

[11] Patent Number: 5,977,416
[45] Date of Patent: Nov. 2, 1999

[54] DEHYDRATION CATALYST AND PROCESS FOR PRODUCING A MONOALKYLETHER OF A DIHYDRIC PHENOLIC COMPOUND USING SAME

[75] Inventors: Tokuo Matsuzaki; Tsunemi Sugimoto; Yasuo Nakamura; Takumi Manabe, all of Ube, Japan

[73] Assignee: Ube Industries, Ltd., Ube, Japan

[21] Appl. No.: 09/058,327

[22] Filed: Apr. 9, 1998

[30] Foreign Application Priority Data

Apr. 15, 1997 [JP] Japan .................. 9-097148
Apr. 15, 1997 [JP] Japan .................. 9-097149

[51] Int. Cl.$^6$ ............ C07C 41/00; C07C 45/00; C07C 27/26; C07C 213/00
[52] U.S. Cl. ............ 568/651; 568/477; 568/922; 568/916; 568/360
[58] Field of Search .................. 568/477, 922, 568/916, 360, 651

[56] References Cited

U.S. PATENT DOCUMENTS 5,658,844  8/1997  Hippel et al. ............ 568/651

FOREIGN PATENT DOCUMENTS

| 0 726092 | 8/1996 | European Pat. Off. . |
| 0 792859 | 9/1997 | European Pat. Off. . |
| 0873786 | 10/1998 | European Pat. Off. . |
| 827803 | 1/1952 | Germany . |
| 51-108026 | 9/1976 | Japan . |
| 53-12826 | 2/1978 | Japan . |
| 53-65837 | 6/1978 | Japan . |
| 4-341345 | 11/1992 | Japan . |
| 52152889 | 12/1997 | Japan . |
| 10-286464 | 10/1998 | Japan . |
| 9801669 | 10/1998 | Norway . |

OTHER PUBLICATIONS

Chemical Abstract 55–7336 1961.
Masloboino–Zhirovaya Prom. 26, No. 10, 24 (1960).
Journal of the Chemical Society of Japan, 12, 2331 (1985).

*Primary Examiner*—Louise N. Leary
*Attorney, Agent, or Firm*—Burgess, Ryan and Wayne

[57] ABSTRACT

A dehydration catalyst useful for producing a monoalkylether of dihydric phenolic compound by a dehydration reaction of a dihydric phenolic compound with a lower alkyl alcohol with a high conversion at a high selectivity, comprises at least one inorganic substance of the empirical formula (I):

$$Al_a P_b Ti_c Si_d X_e O_f \qquad (I)$$

wherein X represents a member selected from the group consisting of (1) an antimony and/or a bismuth atom, and (2) a sulfur atom, a, b, c, d, e and f respectively represent the numbers of Al, P, Ti, Si, X and O atoms, the atomic ratio a:b is 1:1.0 to 1.9, the atomic ratio a:c is 1:0.05 to 0.5, the atomic ratio a:d is 1:0.05 to 0.2, the atomic ratio a:e is 1:0.01 to 0.3 when X represents antimony and/or bismuth atom and 1:0.004 to 0.015 when X represents a sulfur atom, and the atomic ratio a:f is 1:4.1 to 8.4.

9 Claims, No Drawings

DEHYDRATION CATALYST AND PROCESS FOR PRODUCING A MONOALKYLETHER OF A DIHYDRIC PHENOLIC COMPOUND USING SAME

BACKGROUND OF THE INVENTION

1. Field of the Invention

The present invention relates to a dehydration catalyst and a process for producing a monoalkylether of a dihydric phenolic compound using the same. More particularly, the present invention relates to a dehydration catalyst having an enhanced catalytic activity for gas phase dehydration reactions, for example, gas phase etherification and esterification reactions, and a satisfactory mechanical strength, and a process for producing a monoalkylether of a dihydric phenolic compound by dehydration-reacting a dihydric phenolic compound with a lower alkyl alcohol in the gas phase in the presence of the above-mentioned catalyst, with a high conversion at a high selectivity. The monoalkylether of the dihydric phenolic compound is useful as a starting material for the production of perfumes, scents, essences and medicines.

2. Description of the Related Art

Processes for producing a monoalkylether of a dihydric phenolic compound by a gas phase etherification reaction or a gas phase esterification reaction, particularly a gas phase dehydration reaction of a dihydric phenolic compound with a lower alkyl alcohol are known in (1) Chem. Abs., 55–7336 (1961) and Masloboino-Zhirovaya Prom., 26, 10, 24 (1960), wherein a catalyst comprising phosphoric acid and boron is used, (2) Japanese Examined Patent Publication No. 53–35,062, No. 55–33,658 and No. 53–6618, wherein a catalyst comprising aluminum, phosphorus, boron and oxygen is used, (3) Journal of The Chemical Society of Japan, 12, 2331 (1985) and Japanese Examined Patent Publication No. 56–25,213, wherein a kaolin catalyst is used, and (4) Japanese Unexamined No. 4-341,345 in which a catalyst comprising aluminum, phosphorus, titanium, silicon and oxygen is used.

The above-mentioned process (1) is disadvantageous in that the target product, for example, guaiacol, is produced at an unsatisfactory selectivity of about 80 to 90% and, due to a decrease in the content of a $BPO_4$ component in the catalyst during the reaction, the catalyst activity life is very short.

The process (2) is disadvantageous in that the catalytic activity and mechanical strength of the catalyst gradually decrease.

The process (3) is unsatisfactory in that the target product is produced at an insufficient selectivity of about 80%.

The process (4) uses a catalyst having enhanced catalytic activity and mechanical strength. However, since a dihydric phenolic compound having a high boiling temperature is used as a starting material, the collection of the target product from the reaction mixture needs a large amount of energy, and thus, in industry, a new type of catalyst having a further enhanced catalytic activity is strongly demanded.

SUMMARY OF THE INVENTION

An object of the present invention is to provide a catalyst, for dehydration reactions in gas phase etherification or gas phase esterification processes, having an enhanced catalytic activity and mechanical strength, and a process for producing a monoalkyl ether of a dihydric phenolic compound with a high conversion at a high selectivity by a dehydration reaction of a dihydric phenolic compound with a lower alkyl alcohol in the presence of the above-mentioned catalyst.

The above-mentioned object can be attained by the catalyst and process of the present invention.

The catalyst of the present invention for a dehydration reaction comprises at least one inorganic compound of the empirical formula (I):

  (I)

wherein X represents at least one member selected from the group consisting of (1) at least one selected from antimony and bismuth atoms, and (2) sulfur atom, a, b, c, d, e and f respectively represent the numbers of Al, P, Ti, Si, X and O atoms, the atomic ratio a:b is 1:1.0 to 1.9, the atomic ratio a:c is 1:0.05 to 0.5, the atomic ratio a:d is 1:0.05 to 0.2, the atomic ratio a:e is 1:0.01 to 0.3 when X represents at least one member selected from the group consisting of antimony and bismuth atoms and 1:0.004 to 0.015 when X represents a sulfur atom, and the atomic ratio a:f is 1:4.1 to 8.4.

The process of the present invention for producing a monoalkyl ether of a dihydric phenol compound, comprises: subjecting a reaction feed comprising a dihydric phenol compound and a lower alkyl alcohol to a dehydration reaction in the gas phase in the presence of a dehydration catalyst comprising at least one inorganic compound of the empirical formula (I):

  (I)

wherein X represent at least one member selected from the group consisting of (1) antimony and bismuth atoms, and (2) a sulfur atom, a, b, c, d, e and f respectively represent the numbers of Al, P, Ti, Si, X and 0 atoms, the atomic ratio a:b is 1:1.0 to 1.9, the atomic ratio a:c is 1:0.05 to 0.5, the atomic ratio a:d is 1:0.05 to 0.2, the atomic ratio a:e is 1:0.01 to 0.3 when X represents at least one member selected from the group consisting of antimony and bismuth atoms and 1:0.004 to 0.015 when X represents a sulfur atom, and the atomic ratio a:f is 1:4.1 to 8.4.

DESCRIPTION OF THE PREFERRED EMBODIMENTS

The dehydration catalyst of the present invention comprises at least one inorganic compound of the empirical formula (I):

  (I)

wherein X represent a member selected from the group consisting of consisting of (1) at least one member selected from the group consisting of antimony and bismuth atoms, and (2) sulfur atom, a, b, c, d, e and f respectively represent the numbers of Al, P, Ti, Si, X and O atoms, the atomic ratio a:b is 1:1.0 to 1.9, the atomic ratio a:c is 1:0.05 to 0.5, the atomic ratio a:d is 1:0.05 to 0.2, the atomic ratio a:e is 1:0.01 to 0.3 when X represents at least one member of the group consisting of antimony and bismuth atoms and 1:0.004 to 0.015 when X represents a sulfur atom, and the atomic ratio a:f is 1:4.1 to 8.4.

The element represented by X in the empirical formula (I) will be referred to as a catalytic activity-controlling component element hereinafter.

In the catalyst of the present invention, when the phosphorus atoms are present in an amount less than 1.0 atom per atom of aluminum, the resultant catalyst exhibits an unsatisfactory catalytic activity for the dehydration reaction. Also, when the phosphorus atoms are present in an amount more than 1.9 atoms per atom of aluminum, the resultant catalyst exhibits an unsatisfactory catalytic activity and an insufficient mechanical strength, particularly crushing strength, for practical use. Accordingly, the catalyst of the present invention contains phosphorus in an amount of 1.0 to 1.9 atoms per atom of aluminum.

In the catalyst of the present invention, when the content of titanium atoms is less than 0.05 atoms per atom of aluminum, the resultant catalyst exhibits an unsatisfactory catalytic activity and/or the target product is produced with an unsatisfactory selectivity. Also, when the titanium atom content is more than 0.5 atom per atoms of aluminum, the resultant catalyst exhibits unsatisfactory catalytic activity and mechanical strength, particularly crushing strength. Therefore, the catalyst of the present invention contains titanium atoms in an amount of 0.05 to 0.5 atoms per atom of aluminum.

In the catalyst of the present invention, when the content of silicon atoms is less than 0.05 atoms per atom of aluminum, the resultant catalyst exhibits unsatisfactory catalytic activity and mechanical strength, particularly crushing strength. Also, when the silicon atom content is more than 0.2 atoms per atom of aluminum, the resultant catalyst exhibits unsatisfactory catalytic activity. Therefore, the catalyst of the present invention contains silicon atoms in an amount of 0.05 to 0.2 atoms per atom of aluminum.

In the catalyst of the present invention, when the catalytic activity-controlling component consists of bismuth and/or antimony, and the total content of antimony and bismuth atoms is less than 0.01 atoms per atom of aluminum the resultant catalytic activity-controlling component does not contribute to enhancing the catalytic activity of the catalyst. Also, when the total content of antimony and bismuth is more than 0.3 atoms per atom of aluminum, the resultant catalyst exhibits unsatisfactory catalytic activity. Therefore, the catalyst of the present invention contains the catalytic activity-controlling component consisting of antimony and/or bismuth in a total amount of 0.01 to 0.3 atoms per atom of aluminum.

In the catalyst of the present invention, when the catalytic activity-controlling component consists of sulfur and the content of sulfur atoms is less than 0.004 atoms per atom of aluminum, the catalytic activity of the resultant catalyst is not enhanced, and when the sulfur atoms content is more than 0.015 atom per atom of aluminum, the resultant catalyst exhibits an unsatisfactory catalytic activity. Therefore, in the catalyst of the present invention, the content of the catalytic activity-controlling component consisting of sulfur atoms is adjusted to 0.004 to 0.015 atoms per atom of aluminum.

In the catalyst of the present invention, the content of oxygen atoms is adjusted to 4.1 to 8.4 atoms per atom of aluminum. When the catalytic activity-controlling component consists of antimony and/or bismuth atoms, the oxygen atom content is preferably 4.2 to 8.4 atoms per atom of aluminum. Also, when the catalytic activity controlling component consists of sulfur atoms, the oxygen atom content is preferably 4.1 to 7.0 atoms per atom of aluminum.

The catalyst of the present invention can be prepared, for example, by mixing an aluminum-containing substance with a phosphorus-containing substance, a titanium-containing substance, a silicon-containing substance, and a catalytic activity-controlling component element(s) (bismuth and/or antimony or sulfur)-containing substance in an atomic ratio of aluminum to phosphorus 1:1.0 to 1.9, an atomic ratio of aluminum to titanium of 1:0.05 to 0.5, and an atomic ratio of aluminum to silicon of 1:0.05 to 0.2, and in an atomic ratio of aluminum to bismuth and/or antimony of 1:0.01 to 0.3 or of aluminum to sulfur of 1:0.004 to 0.015; admixing the resultant mixture with water in an amount of 0.1 to 2.0 parts by weight per part by weight of the mixture; heating the resultant admixture at a temperature of 70° to 110° C., preferably for a time of 4 to 20 hours, while stirring the admixture; drying the heated admixture at a temperature of 90° to 120° C. in an oxygen-containing gas atmosphere, for example, in an ambient air atmosphere;

and then calcining the dried admixture at a temperature of 300° to 600° C. in an oxygen-containing gas atmosphere, for example, in an ambient air atmosphere, preferably for a time of 1 to 10 hours.

The calcining procedure is preferably carried out by forming the dried admixture into particles by using a granulator or pelletizer, and then calcining the particles at the temperature of 300° C. to 600° C. for 1 to 10 hours.

The catalyst particles produced by the above-mentioned procedures preferably have an average particle size of 0.5–20 mm, more preferably 1 to 10 mm, and can form a fixed bed or a mobile bed in a reactor for the dehydration reaction. Also, the catalyst particles preferably have a total pore volume of about 0.3 to 0.6 ml/g and a BET specific surface area of about 30 to 50 $m^2/g$.

In the preparation of the catalyst of the present invention, the aluminum-containing substance comprises at least one member selected from the group consisting of an oxide, hydroxide, carbonate and nitrate of aluminum; the phosphorus-containing substance comprises at least one member selected from the group consisting of orthophosphoric acid, pyrophosphoric acid, methaphosphoric acid, tetraphosphoric acid, polymethaphosphoric acid, phosphoric anhydride, and phosphoric acid esters (for example, trimethyl phosphate and triethyl phosphate); the titanium-containing substance comprises at least one member selected from the group consisting of titanium oxides, for example, titania and titania sol, and titanium hydroxides; the silicon-containing substance comprises at least one member selected from the group consisting of oxides, nitrides, carbides, of silicon for example, silica sol, silica gel, $Si_3N_4$, and SiC and organic silicon compounds; and the catalytic activity-controlling component element-containing substance comprises at least one member selected from the group consisting of (1) oxides, hydroxides, alkoxides and organic compounds of antimony, for example, trimethoxy antimony, triethoxy antimony, triethyl antimony and oxides, hydroxides, organic acid salts and organic compounds of bismuth (for example, bismuth acetate and triphenyl bismuth), or (2) sulfuric acid, and sulfuric acid salts of aluminum and titanium.

The sulfur-containing substance may be selected from sulfur-containing catalyst materials, for example, sulfur-containing titania sol.

The catalyst of the present invention comprises no $BPO_4$ and thus is free from the phenomenon that the content of $BPO_4$ in the catalyst decreases during the reaction and the catalytic activity of the catalyst is greatly reduced within a short time. Therefore, the catalytic activity of the catalyst of the present invention can be retained at a satisfactory level substantially without a deterioration thereof over a long period of employment. However, when the catalytic activity is reduced due to adhesion of carbon or organic substances, the catalyst can be regenerated by calcining in an oxygen-containing gas atmosphere, for example, in an ambient air atmosphere.

The catalyst of the present invention is useful as a dehydration catalyst for gas phase etherification and esterification reactions, particularly for a gas phase etherification reaction of a dihydric phenolic compound with a lower alkyl alcohol to produce a monoalkyl ether of the dihydric phenolic compound.

The dehydration reaction of the dihydric phenolic compound with the lower alkyl alcohol is preferably carried out by feeding a reaction feed comprising the dihydric phenolic compound and the lower alkyl alcohol to a reactor packed with the catalyst of the present invention, and heating the reaction feed in the reactor at a temperature of 200° to 400° C., more preferably 230° to 350° C. under ambient atmospheric pressure or a gauge pressure of, for example, 1 to 50 kg/cm$^2$.

In the above-mentioned process, the dihydric phenolic compound and the lower alkyl alcohol are heat-vaporized separately from each other or together with each other in a vaporizer (preferably having a pre-heating section and a vaporizing section) and fed together with an inert carrier gas, for example, nitrogen gas, into a reactor.

In this reaction, the dihydric phenolic compound in the gas phase is preferably fed in a feeding rate of 0.01 to 10 g/hr, more preferably 0.05 to 1.0 g/hr per ml of the dehydration catalyst, and the lower alkyl alcohol is used in an amount of about 1 to 50 moles, more preferably about 2 to 15 moles per mole of the dihydric phenolic compound.

The reaction for the gas phase dehydration reaction is preferably selected from reactors having a fixed catalyst bed or a fluidized catalyst bed through which the gas phase reaction feed flows.

The dihydric phenolic compound usable for the process of the present invention is preferably selected from unsubstituted dihydric phenolic compounds, for example, catechol, hydroquinone and resorcinol, and substituted dihydric phenolic compounds having at least one substituted selected from the group consisting of an alkyl group having 1 to 30 carbon atoms and halogen atoms, for example, alkyl-substituted dihydric phenolic compounds, for example, 4-methyl catechol, 2-methyl catechol, and 2-methyl hydroquinone, and hydrogen-substituted dihydric phenolic compounds for example, 4-chlorocatechol, 2-chlorocatechol and 2-chlorohydroquinone.

The lower alkyl alcohol usable for the process of the present invention is preferably selected from aliphatic mono alkyl alcohols having 1 to 6 carbon atoms, more preferably 1 to 4 carbon atoms, for example, methyl alcohol, ethyl alcohol, n-propyl alcohol, isopropyl alcohol, n-butyl alcohol and isobutyl alcohol.

In the gas phase catalytic dehydration procedure in accordance with the process of the present invention, at least one phosphorus compound is optionally added to the reaction feed comprising the dihydric phenolic compound and the lower alkyl alcohol to prevent the reduction in the catalytic activity of the catalyst. The phosphorus compound may be directly fed continuously or intermittently into the reactor during the reaction. Alternatively, the phosphorus compound is added to the reaction feed before the reaction.

Also, in the gas phase dehydration reaction procedure, at least one boron compound is optionally fed together with the phosphorus compound to the reactor, to prevent the reduction in the catalytic activity of the catalyst.

The phosphorus compound is preferably employed in an amount of 0.01 to 2% by weight, more preferably 0.05 to 1% by weight based on the total weight of the reaction feed comprising the dihydric phenolic compound and the lower alkyl alcohol.

The boron compound is preferably employed in an amount of 0.01 to 2% by weight, more preferably 0.05 to 1% by weight, based on the total weight of the reaction feed.

The phosphorus compound usable for the process of the present invention is preferably selected from trialkyl phosphates wherein each of the alkyl group groups has 1 to 6 carbon atoms, for example, trimethyl phosphate and triethyl phosphate, and boron phosphate.

The boron compound usable for the process of the present invention is preferably selected from the group consisting of boric acid and trialkyl borates in which each of the alkyl groups has 1 to 6 carbon atoms.

The catalyst of the present invention, is useful for gas phase etherification and esterification processes wherein a dehydration reaction is carried out.

In the process of the present invention, a dihydric phenolic compound is reacted with a lower alkyl alcohol in the gas phase in the presence of the dehydration catalyst as mentioned above, to produce a monoalkylether of dihydric phenolic compound, for example, guaiacol (catechol monomethylether), catechol monoethylether and hydroquinone monomethylether. The target compound can be easily collected by cooling a reaction mixture gas delivered from the reactor to a temperature of, for example, 40° C. or less. The collected target compound is optionally refined, for example, by distillation.

EXAMPLES

The present invention will be further illustrated by the following examples.

In the examples, the conversion of a dihydric phenolic compound, for example, catechol, is the percentage of a consumed portion of the dihydric phenolic compound based on the total amount of the dihydric phenolic compound changed into reaction, the selectivity of the resultant target compound, for example, guaiacol, is a percentage of the resultant target compound based on the amount of the consumed dihydric phenolic compound, and the selectivity of a dialkylether of the dihydric phenolic compound, for example, veratrol, is a percentage of the dialkylether of the dihydric phenolic compound based on the amount of the consumed dihydric phenolic compound.

The above-mentioned conversion and selectivities were calculated on a molar basis.

Example 1
(Preparation of catalyst (A))

A mixture of 327 g of aluminum hydroxide with 58.6 g of bismuth oxide and 877 g of water was stirred at a temperature of 100° C. for 14 hours while refluxing. To the mixture, 129 g of a titania sol containing 26% by weight of titanium dioxide and 144 g of a silica sol containing 30% by weight of silica were added, and 531.6 g of an 85 weight % orthophosphoric acid were added dropwise at an adding rate of 12 g/min. The resultant mixture was stirred at a temperature of 100° C. for 8 hours, while refluxing.

The resultant white paste was concentrated and then dried at a temperature of 120° C. for 24 hours in an ambient air atmosphere, and the resultant dried substance was pulverized into fine particles and passed through a 16 mesh or smaller size sieve. The fine particles were molded into circular cylinder-shaped pellets having a diameter of 6 mm and a length of 6 mm, and calcined in an ambient air atmosphere at a temperature of 400° C. for 5 hours.

In the resultant catalyst (A), the atomic ratio of aluminum to bismuth was 1:0.06. The atomic ratio of the component atoms in the catalyst (A) is shown in Table 1.

The catalyst (A) exhibited a crushing strength equivalent to that of a corresponding comparative catalyst containing no bismuth.

The crush strength measurement was carried out by using a Kiya-type hardness tester, and repeated on 20 catalyst pellets.

The crush strength was represented by a largest crushing load when the 20 catalyst pellets were crushed under load.

EXAMPLE 2
(Preparation of catalyst (B))

A catalyst (B) was prepared by the same procedures as in Example 1, except that the bismuth oxide was replaced by 61.1 g of antimony oxide.

In the resultant catalyst (B), the atomic ratio of aluminum to antimony was 1:0.10. The atomic ratio of the catalyst (B) is shown in Table 1. The pellets of the catalyst (B) exhibited a crushing strength similar to that of a corresponding comparative catalyst pellets containing no antimony.

Example 3
(Preparation of catalyst (C))

A catalyst (C) was prepared by the same procedures as in Example 1, except that the bismuth oxide was replaced by 122.2 g of antimony oxide.

In the resultant catalyst (C), the atomic ratio of aluminum to antimony was 1:0.19. The atomic ratio of the catalyst (C) is shown in Table 1. The pellets of the catalyst (C) exhibited a crushing strength similar to that of a corresponding comparative catalyst pellets containing no antimony.

Comparative Example 1
(Preparation of catalyst (D))

A catalyst (D) was prepared by the same procedures as in Example 1, except that no bismuth oxide was employed. The atomic ratio of the catalyst (D) is shown in Table 1. The pellets of the catalyst (D) exhibited a crushing strength of 6.30 kg.

TABLE 1

| | | Item | | | | | | |
|---|---|---|---|---|---|---|---|---|
| | | Atomic ratio | | | | | | |
| Example No. | Catalyst | Al | P | Ti | Si | Bi | Sb | O |
| Example 1 | A | 1 | 1.1 | 0.1 | 0.17 | 0.06 | — | 4.88 |
| 2 | B | 1 | 1.1 | 0.1 | 0.17 | — | 0.10 | 4.94 |
| 3 | C | 1 | 1.1 | 0.1 | 0.17 | — | 0.19 | 5.08 |
| Comparative Example 1 | D | 1 | 1.1 | 0.1 | 0.17 | — | — | 4.79 |

Example 4
(Production of guaiacol by gas phase catalytic dehydration reaction)

The catalyst (A) pellets prepared in Example 1 were packed in an amount of 18 ml in a heat resistant glass (PIREX) reactor tube having a diameter of 30 mm and a length of 400 mm, to form a catalyst layer. The catalyst layer was heated, and when the temperature of the catalyst layer reached 300° C., a mixture of 1 mole of catechol with 3.44 moles of methyl alcohol was evaporated in an evaporator under ambient atmospheric pressure and fed into the catalyst layer at a space velocity (WHSV) of 0.3 kg/liter of catalyst-hour, together with a nitrogen carrier gas, for 14 hours.

The resultant reaction mixture gas delivered from the reactor tube was cooled to room temperature by water, to collect a reaction product.

The reaction product was subjected to a gas chromatographic analysis. As a result, it was confirmed that the conversion of catechol was 78.5%, the selectivity of guaiacol was 98.3% and the selectivity of veratrol was 1.0%.

The analysis result is shown in Table 2.

Example 5

The same guaiacol production procedures from catechol as in Example 4 were carried out, except that the catalyst (A) was replaced by 18 ml of the catalyst (B) prepared in Example 2.

The analysis result is shown in Table 2.

Example 6

The same guaiacol production procedures from catechol as in Example 4 were carried out, except that the catalyst (A) was replaced by 18 ml of the catalyst (C) prepared in Example 3.

The analysis result is shown in Table 2.

Comparative Example 2

The same guaiacol production procedures from catechol as in Example 4 were carried out, except that the catalyst (A) was replaced by 18 ml of the catalyst (D) prepared in Comparative Example 1.

The analysis result is shown in Table 2.

TABLE 2

| | | Item | | |
|---|---|---|---|---|
| | | Analysis result | | |
| Example No. | | Conversion of catechol (%) | Selectivity of guaiacol (%) | Selectivity of veratrol (%) |
| Example 4 | A | 78.5 | 98.3 | 1.0 |
| 5 | B | 79.9 | 98.1 | 0.3 |
| 6 | C | 85.3 | 97.9 | 1.1 |
| Comparative Example 2 | D | 64.4 | 98.7 | 0.8 |

Example 7
(Preparation of catalyst (E))

A mixture of 327 g of aluminum hydroxide with 877 g of water was stirred at a temperature of 100° C. for 14 hours while refluxing. To the mixture, 129 g of a titania sol containing 26% by weight of titanium dioxide and 1.08% by weight, in terms of $SO_3$, of a sulfur-containing component, and 144 g of a silica sol containing 30% by weight of silica were added, and 531.6 g of an 85 weight % orthophosphoric acid were added dropwise at an adding rate of 12 g/min. The resultant mixture was stirred at a temperature of 100° C. for 8 hours, while refluxing.

The resultant white paste was concentrated and then dried at a temperature of 120° C. for 24 hours in ambient air atmosphere, and the resultant dried substance was pulverized into fine particles and passed through a 16 mesh or smaller size sieve. The fine particles were molded into circular cylinder-shaped pellets having a diameter of 6 mm and a length of 6 mm, and calcined in ambient air atmosphere at a temperature of 400° C. for 5 hours.

In the resultant catalyst (E), the atomic ratio of aluminum to sulfur was 1:0.0042. The atomic ratio of the component atoms in the catalyst (E) is shown in Table 3.

The catalyst (E) exhibited a crushing strength equivalent to that of a corresponding comparative catalyst containing no sulfur.

The crush strength measurement was carried out by using a Kiya-type hardness tester, and repeated on 20 catalyst pellets.

The crush strength was represented by a largest crushing load when the 20 catalyst pellets were crushed under load.

Example 8
(Preparation of catalyst (F))

A catalyst (F) was prepared by the same procedures as in Example 7 except that, as a titanium and sulfur-containing substance, 129 g of a titania sol containing 26% by weight of titanium dioxide and 3.0% by weight, in terms of $SO_3$, of a sulfur-containing component was employed.

In the resultant catalyst (F), the atomic ratio of aluminum to sulfur was 1:0.012. The atomic ratio of the catalyst (F) is shown in Table 3.

The catalyst (F) exhibited a crushing strength equivalent to that of the corresponding comparative catalyst containing no sulfur.

Example 9
(Preparation of catalyst (G))

A catalyst (G) was prepared by the same procedures as in Example 7 except that, as a titanium-containing substance, a titania sol prepared by hydrolyzing 119 g of titanium tetraisopropoxide with a mixture of 300 g of ethyl alcohol with 200 g of water, and evaporating away ethyl alcohol was employed, and as a sulfur-containing substance, 3.2 g of a 96 weight % sulfuric acid was employed.

In the resultant catalyst (G), the atomic ratio of aluminum to sulfur was 1:0.0075. The atomic ratio of the elements in the catalyst (G) is shown in Table 3.

The catalyst (G) exhibited a crushing strength equivalent to that of the corresponding comparative catalyst containing no sulfur.

Comparative Example 3
(Preparation of catalyst (H))

A catalyst (H) was prepared by the same procedures as in Example 7, except that as a titanium-containing substance, a titania sol prepared by hydrolyzing 119 g of titanium tetraisopropoxide with a mixture of 300 g of ethyl alcohol with 200 g of water, and evaporating away ethyl alcohol and no sulfur-containing substance was used.

In the resultant catalyst (H), the amount of sulfur was 0.0001 atom or less per atom of aluminum. The atomic ratio of the elements in the catalyst (H) are shown in Table 3. The catalyst (H) exhibited a crushing strength of 6.30 kg.

Comparative Example 4
(Preparation of catalyst (I))

A catalyst (I) was prepared by the same procedures as in Example 7, except that as a titanium and sulfur-containing substance, 129 g of titania sol containing 26% by weight of titanium dioxide and 4.87% by weight, in terms of $SO_3$, of a sulfur-containing component was employed.

In the obtained catalyst (I), the atomic ratio of aluminum to sulfur was 1:0.019. The atomic ratio of the elements in the catalyst (I) is shown in Table 3.

The catalyst (I) exhibited a crushing strength of 6.21 kg.

TABLE 3

| Example No. | | Catalyst | Atomic ratio | | | | | |
|---|---|---|---|---|---|---|---|---|
| | | | Al | P | Ti | Si | S | O |
| Example | 7 | E | 1 | 1.1 | 0.1 | 0.17 | 0.0042 | 4.53 |
| | 8 | F | 1 | 1.1 | 0.1 | 0.17 | 0.012 | 4.56 |
| | 9 | G | 1 | 1.1 | 0.1 | 0.17 | 0.0075 | 4.54 |
| Comparative | 3 | H | 1 | 1.1 | 0.1 | 0.17 | <0.0001 | 4.52 |
| Example | 4 | I | 1 | 1.1 | 0.1 | 0.17 | 0.019 | 4.58 |

Example 10
(Production of guaiacol by gas phase catalytic dehydration reaction)

The catalyst (E) pellets prepared in Example 7 was packed in an amount of 18 ml in a heat resistant glass (PIREX) reactor tube having a diameter of 30 mm and a length of 400 mm, to form a catalyst layer. The catalyst layer was heated, and when the temperature of the catalyst layer reached 300° C., a mixture of 1 mole of catechol with 3.44 moles of methyl alcohol was evaporated in an evaporator under ambient atmospheric pressure and fed into the catalyst layer at a space velocity (WHSV) of 0.3 kg/liter of catalyst-hour, together with a nitrogen carrier gas, for 14 hours.

The resultant reaction mixture gas delivered from the reactor tube was cooled to room temperature by water, to collect a reaction product.

The reaction product was subjected to a gas chromatographic analysis. As a result, it was confirmed that the conversion of catechol was 70.4%, the selectivity of guaiacol was 97.8% and the selectivity of veratrol was 1.1%.

The analysis result is shown in Table 4.

Example 11

The same guaiacol production procedures, from catechol, as in Example 10 were carried out, except that the catalyst (E) was replaced by 18 ml of the catalyst (F) prepared in Example 8.

The analysis result is shown in Table 4.

Example 12

The same guaiacol production procedures, from catechol, as in Example 10 were carried out, except that the catalyst (E) was replaced by 18 ml of the catalyst (G) prepared in Example 9.

The analysis result is shown in Table 4.

Comparative Example 5

The same guaiacol production procedures, from catechol, as in Example 10 were carried out, except that the catalyst (E) was replaced by 18 ml of the catalyst (H) prepared in Comparative Example 3.

The analysis result is shown in Table 4.

Comparative Example 6

The same guaiacol production procedures, from catechol, as in Example 10 were carried out, except that the catalyst (E) was replaced by 18 ml of the catalyst (I) prepared in Comparative Example 4.

The analysis result is shown in Table 4.

TABLE 4

| Example No. | | Catalyst | Conversion of catechol (%) | Selectivity of guaiacol (%) | Selectivity of veratrol (%) |
|---|---|---|---|---|---|
| Example | 10 | E | 70.4 | 97.8 | 1.1 |
|  | 11 | F | 75.9 | 97.6 | 1.3 |
|  | 12 | G | 73.3 | 97.5 | 1.1 |
| Comparative | 5 | H | 56.8 | 97.7 | 1.1 |
| Example | 6 | I | 24.2 | 98.6 | 1.0 |

The catalyst of the present invention exhibits a high catalytic activity for gas phase dehydration reactions of gas phase etherification and esterification processes and a satisfactory mechanical strength. Also, by using the catalyst of the present invention, a monoalkylether of dihydric phenolic compound can be produced by a gas phase dehydration reaction of a dihydric phenolic compound with a lower alkyl alcohol with a high conversion of the dihydric phenolic compound at a high selectivity of the target compound.

We claim:

1. A catalyst for dehydration reactions comprising at least one inorganic substance of the empirical formula (I):

$$Al_a P_b Ti_c Si_d X_e O_f \qquad (I)$$

wherein X represents a member selected from the group consisting of (1) at least one atom selected from antimony and bismuth atoms, and (2) a sulfur atom, a, b, c, d, e and f respectively represent the numbers of Al, P, Ti, Si, X and O atoms, the atomic ratio a:b is 1:1.0 to 1.9, the atomic ratio a:c is 1:0.05 to 0.5, the atomic ratio a:d is 1:0.05 to 0.2, the atomic ratio a:e is 1:0.01 to 0.3 when X represents as least one atom selected from the group consisting of antimony and bismuth atoms and 1:0.004 to 0.015 when X represents a sulfur atom, and the atomic ratio a:f is 1:4.1 to 8.4.

2. The dehydration catalyst as claimed in claim 1, wherein in the empirical formula (I), X represents at least one atom selected from the group consisting of antimony and bismuth atoms, the atomic ratio a:e is 1:0.01 to 0.3, and the atomic ratio a:f is 1:4.2 to 8.4.

3. The dehydration catalyst as claimed in claim 1, wherein in the empirical formula (I), X represents a sulfur atom, the atomic ratio a:e is 1:0.004 to 0.015, and the atomic ratio a:f is 1:4.1 to 7.0.

4. The dehydration catalyst as claimed in claim 1, prepared by mixing substances respectively containing Al, P, Ti, Si and the element represented by X in the empirical formula (I) with each other in the atomic ratios a:b, a:c, a:d and a:e as mentioned above; admixing the mixture with water in an amount of 0.1 to 2.0 parts by weight per part by weight of the mixture; heating the admixture at a temperature of 70° to 110° C., while stirring; drying the heated admixture at a temperature of 90° to 120° C.; and calcining the dried admixture at a temperature of 300° to 600° C. in an oxygen-containing gas atmosphere.

5. The dehydration catalyst as claimed in claim 4, wherein the Al-containing substance comprises at least one member selected from the group consisting of an oxide, hydroxide, carbonate and nitrate of aluminum;

the P-containing substance comprises at least one member selected from the group consisting of orthophosphoric acid, pyrophosphoric acid, methaphosphoric acid, tetraphosphoric acid, polymethaphosphoric acid, phosphoric anhydride, and phosphoric acid esters;

the Ti-containing substance comprises at least one member selected from the group consisting of titanium oxides and titanium hydroxides;

the Si-containing substance comprises at least one member selected from the group consisting of oxides, nitrides and carbides of silicon; and the element-containing substance comprises (1) at least one member selected from the group consisting of oxides, hydroxides, alkoxides and organic compounds of antimony, and oxides, hydroxides and organic compounds of bismuth, or (2) sulfuric acid, and sulfuric acid salts of aluminum and titanium.

6. A process for producing a monoalkyl ether of a dihydric phenolic compound, comprising;

subjecting a reaction feed comprising a dihydric phenol compound and a lower alkyl alcohol to a dehydration reaction in the gas phase in the presence of a dehydration catalyst comprising at least one inorganic compound of the empirical formula (I):

$$Al_a P_b T_{ic} Si_d X_e O_f \qquad (I)$$

wherein X represent a member selected from the group consisting of (1) at least one atom selected from the group consisting of antimony and bismuth atoms, and (2) a sulfur atom, a, b, c, d, e and f respectively represent the numbers of Al, P, Ti, Si, X and O atoms, the atomic ratio a:b is 1:1.0 to 1.9, the atomic ratio a:c is 1:0.05 to 0.5, the atomic ratio a:d is 1:0.05 to 0.2, the atomic ratio a:e is 1:0.01 to 0.3 when X represents as least one atom of the group consisting antimony and bismuth atoms and 1:0.004 to 0.015 when X represents a sulfur atom, and the atomic ratio a:f is 1:4.1 to 8.4.

7. The process as claimed in claim 6, wherein in the empirical formula (I), X represents a sulfur atom, the atomic ratio a:e is 1:0.004 to 0.015, and the atomic ratio a:f is 1:4.1 to 7.0.

8. The process as claimed in claim 6, wherein before or during the dehydration reaction, at least one phosphorus compound is added to the reaction feed.

9. The process as claimed in claim 8, wherein the phosphorus compound is present in an amount of 0.01 to 2% by weight based on the total weight of the reaction feed.

* * * * *